(12) United States Patent
West et al.

(10) Patent No.: US 8,696,660 B2
(45) Date of Patent: *Apr. 15, 2014

(54) DEVICES, SYSTEMS AND METHODS FOR TREATING TISSUE REGIONS OF THE BODY

(75) Inventors: Scott H West, Livermore, CA (US); David Huyhn, Santa Clara, CA (US); John W Gaiser, Mountain View, CA (US)

(73) Assignee: Mederi Therapeutics Inc., Norwalk, CT (US)

( * ) Notice: Subject to any disclaimer, the term of this patent is extended or adjusted under 35 U.S.C. 154(b) by 1610 days.

This patent is subject to a terminal disclaimer.

(21) Appl. No.: 11/702,695

(22) Filed: Feb. 6, 2007

(65) Prior Publication Data

US 2007/0161966 A1 Jul. 12, 2007

Related U.S. Application Data

(62) Division of application No. 10/760,433, filed on Jan. 20, 2004, now Pat. No. 7,179,257, which is a division of application No. 09/955,915, filed on Sep. 19, 2001, now Pat. No. 6,699,243.

(51) Int. Cl.
*A61B 18/14* (2006.01)
*A61F 7/00* (2006.01)

(52) U.S. Cl.
USPC .............................................. 606/41; 607/105

(58) Field of Classification Search
USPC ................... 606/41, 42, 45–50; 607/101–105
See application file for complete search history.

(56) References Cited

U.S. PATENT DOCUMENTS

| | | | |
|---|---|---|---|
| 5,334,193 A | 8/1994 | Nardella | |
| 5,370,675 A | 12/1994 | Edwards et al. | |
| 5,454,782 A | 10/1995 | Perkins | |
| 5,588,960 A * | 12/1996 | Edwards et al. | 604/20 |
| 5,658,278 A | 8/1997 | Imran et al. | |
| 5,688,267 A | 11/1997 | Panescu et al. | |
| 6,006,755 A | 12/1999 | Edwards | |
| 6,009,877 A | 1/2000 | Edwards | |
| 6,016,452 A | 1/2000 | Kasevich | |
| 6,044,846 A | 4/2000 | Edwards | |
| 6,056,744 A | 5/2000 | Edwards | |
| 6,092,528 A | 7/2000 | Edwards | |
| 6,254,598 B1 * | 7/2001 | Edwards et al. | 606/41 |
| 6,258,087 B1 | 7/2001 | Edwards et al. | |
| 6,355,031 B1 | 3/2002 | Edwards et al. | |
| 6,405,732 B1 | 6/2002 | Edwards et al. | |

(Continued)

FOREIGN PATENT DOCUMENTS

| | | |
|---|---|---|
| WO | WO 99/35986 | 7/1999 |
| WO | WO 01/05318 | 1/2001 |
| WO | WO 02/28303 | 4/2002 |

*Primary Examiner* — Michael Peffley (57) ABSTRACT

Improved devices, systems and methods for treating a tissue region provide straightforward, yet reliable ways for installing diverse functional components within the confined space of a catheter-based instrument. Methods include providing a manifold body sized to fit within a catheter tube, the manifold body including a single main fluid junction, multiple branch fluid junctions, and a fluid circuit formed within the manifold body to channel fluid flow between the single main fluid junction and the multiple branch fluid junctions, coupling the single main fluid junction to a fluid source or a fluid destination external to the catheter tube, coupling each of the multiple branch fluid junctions individually to a fluid-conveying port on the operative element, and mounting the manifold within the catheter tube.

20 Claims, 12 Drawing Sheets

(56) References Cited

U.S. PATENT DOCUMENTS

| | | |
|---|---|---|
| 6,464,689 B1 | 10/2002 | Qin et al. |
| 6,464,697 B1 | 10/2002 | Edwards et al. |
| 6,506,189 B1 | 1/2003 | Rittman et al. |
| 6,537,272 B2 | 3/2003 | Christopherson et al. |
| 6,544,226 B1 | 4/2003 | Gaiser et al. |
| 6,547,776 B1 | 4/2003 | Gaiser et al. |
| 6,589,238 B2 | 7/2003 | Edwards et al. |
| 6,645,201 B1 | 11/2003 | Utley et al. |
| 6,699,243 B2 | 3/2004 | West et al. |
| 6,733,495 B1 | 5/2004 | Bek et al. |
| 6,783,523 B2 | 8/2004 | Qin et al. |
| 6,790,207 B2 | 9/2004 | Utley et al. |
| 6,802,841 B2 | 10/2004 | Utley et al. |
| 6,989,009 B2 * | 1/2006 | Lafontaine ............... 606/20 |
| 2002/0120262 A1 | 8/2002 | Bek et al. |
| 2002/0151871 A1 | 10/2002 | Gaiser et al. |
| 2002/0162555 A1 | 11/2002 | West et al. |
| 2004/0089313 A1 | 5/2004 | Utley et al. |
| 2005/0004565 A1 * | 1/2005 | Vanney ..................... 606/41 |

* cited by examiner

DEVICES, SYSTEMS AND METHODS FOR TREATING TISSUE REGIONS OF THE BODY

RELATED APPLICATIONS

This application is a divisional of U.S. application Ser. No. 10/760,433, filed Jan. 20, 2004, now U.S. Pat. No. 7,179,257, which is a divisional of U.S. application Ser. No. 09/955,915, filed Sep. 19, 2001, entitled "Devices, Systems and Methods for Treating Tissue Regions of the Body" (now U.S. Pat. No. 6,699,243).

FIELD OF THE INVENTION

The invention is directed to devices, systems and methods for treating tissue regions of the body.

BACKGROUND OF THE INVENTION

Catheter based instruments are widely used to gain access to interior body regions for diagnostic or therapeutic purposes. The size of such instruments are constrained by the need to permit deployment and use within relatively small, confined areas of the body. Still, there is the need for such instruments to carry one or more functional components, e.g., to ablate body tissue and/or to convey fluid into contact with tissue in the targeted tissue region and/or to sense local tissue conditions, etc.

The challenge persists in accommodating the need for small, easily deployed catheter-based instruments with the demand for reliable and robust functionality.

SUMMARY OF THE INVENTION

The invention provides improved devices, systems and methods for treating a tissue region that provide straightforward, yet reliable ways for installing diverse functional components within the confined space of a catheter-based instrument.

One aspect of the invention provides a support assembly for an elongated electrode element. The support assembly comprises at least one spine for holding the elongated electrode element for use. The spine peripherally defines at least one spine lumen. The support assembly also includes an insert carried by the spine. The insert peripherally defines an insert lumen sized to accommodate forward and rearward sliding movement of the elongated electrode element within the spine. The insert includes a distal extension having an outer dimension sized for insertion into the spine lumen. The insert also includes a proximal region having an outer dimension sized to resist insertion into the spine lumen, to thereby define a maximum insertion length for the distal extension into the spine lumen.

In one embodiment, the spine includes a side opening, and the distal extension of the insert includes an open distal end. In this arrangement, the maximum insertion length places the open distal end in desired alignment with the side opening for guiding sliding movement of a distal portion of the elongated electrode element toward the side opening.

In one embodiment, the spine includes an interior ramp that depends from the side opening. In this arrangement, the maximum insertion length locates the open distal end of the insert on the interior ramp for guiding sliding movement of a distal portion of the elongated electrode element toward the side opening.

In one embodiment, the maximum insertion length keeps the distal end of the insert from projecting through the side opening.

Another aspect of the invention provides an electrode assembly. The assembly comprises an elongated electrode element having a distal operative portion. A connector to couple the elongated electrode element to a source of radio frequency energy. The assembly also mounts the elongated electrode element for sliding movement within an insert in a spine, as previously described.

Another aspect of the invention provides a method for making a support assembly for an elongated electrode element. The method provides at least one spine with a lumen for holding the elongated electrode element for use. The method forms a side opening in the spine in communication with the spine lumen. The method also provides an insert for the spine lumen. The insert peripherally defines an insert lumen sized to accommodate forward and rearward sliding movement of the elongated electrode element within the spine. The insert includes a distal extension having an outer dimension sized for insertion into the spine lumen. The insert also includes a proximal region having an outer dimension sized to resist insertion into the spine lumen.

The method inserts the distal extension through the spine lumen and outward beyond the side opening until the proximal region resists further insertion. The method cuts the distal extension flush with the side opening to form an open distal end. The cutting also defines a maximum insertion length for the distal extension.

In one embodiment, the method secures the proximal region of the insert to the spine.

In one embodiment, after performing the cutting step, the method moves the proximal region of the insert a short distance from the spine to withdraw the open distal end into the spine lumen. Afterwards, the method can secure the proximal region of the insert to the spine.

In one embodiment, the method forms an interior ramp that depends from the side opening. In this arrangement, the distal extension is inserted through the spine lumen and outward beyond the side opening along the interior ramp.

In one arrangement, after performing the cutting step, the method moves the proximal region a short distance from the spine to withdraw the open distal end into the spine lumen to rest on the interior ramp. Afterward, the method can secure the proximal region of the insert to the spine.

Another aspect of the invention provides systems and methods for handling fluid to or from an operative element carried by a catheter tube. The systems and methods provide a manifold body sized to fit within the catheter tube. The manifold body includes a single main fluid junction, multiple branch fluid junctions, and a fluid circuit formed within the manifold body to channel fluid flow between the single main fluid junction and the multiple branch fluid junctions. The systems and methods couple the single main fluid junction to a fluid source or a fluid destination external to the catheter tube. The systems and methods couple each of the multiple branch fluid junctions individually to a fluid-conveying port on the operative element. The systems and methods mount the manifold within the catheter tube.

Features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction in various locations in an animal body. For example, the various aspects of the invention have application in procedures requiring treatment of sphincters and adjoining tissue regions in the body, or hemorrhoids, or incontinence, or restoring compliance to or otherwise tightening interior tissue or muscle regions. The systems and methods that embody features of the invention are also adaptable for use with systems and surgical techniques that are not necessarily catheter-based.

The systems and methods are particularly well suited for treating dysfunctions in the upper gastrointestinal tract, e.g., in the lower esophageal sphincter and adjacent cardia of the stomach. For this reason, the systems and methods will be described in this context. Still, it should be appreciated that the disclosed systems and methods are applicable for use in treating other dysfunctions elsewhere in the body, which are not necessarily sphincter-related.

I. Overview

Figure 1:
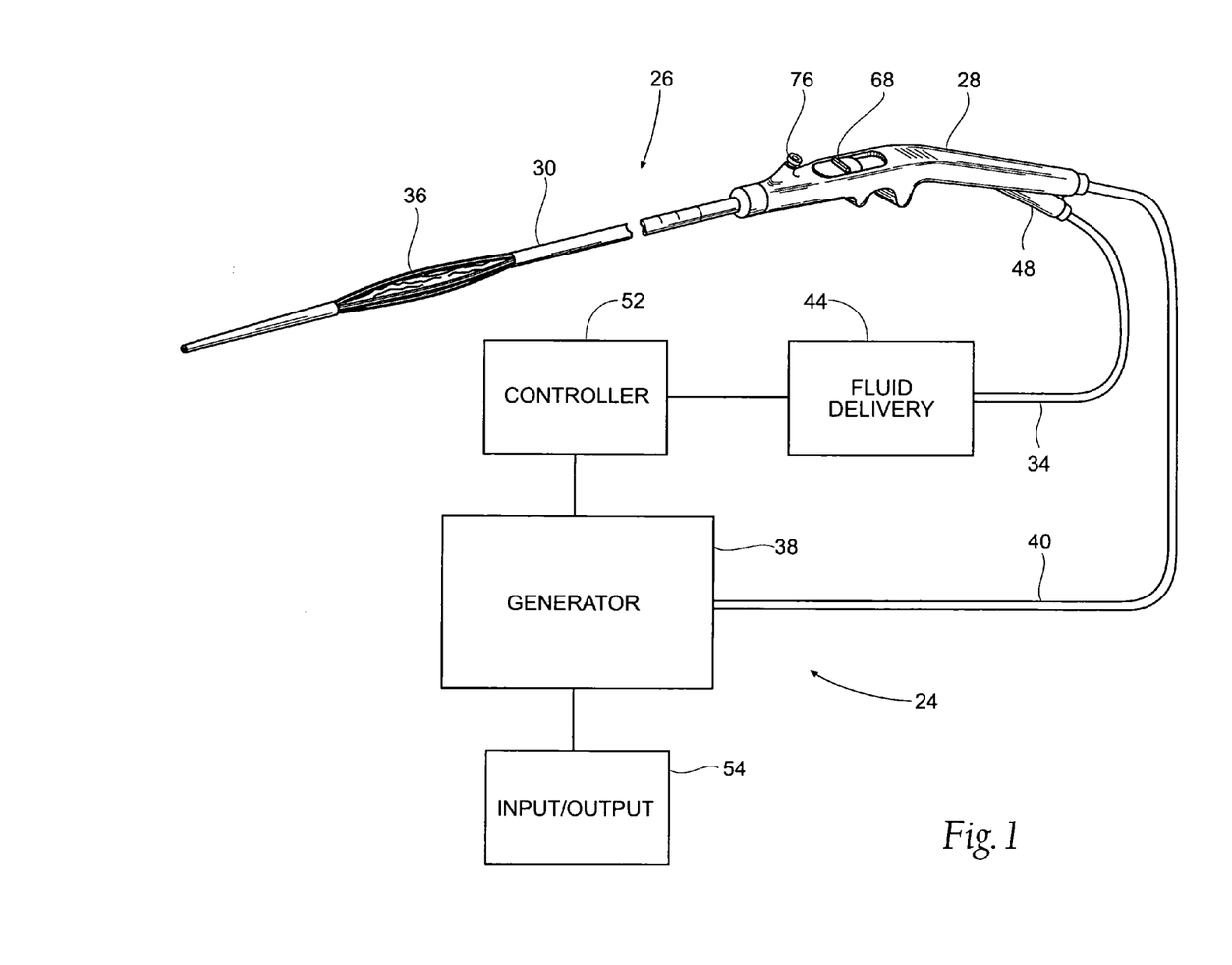
FIG. 1 is a schematic view of a system for treating tissue that includes a treatment device that embodies features of the invention.

A tissue treatment device 26 is shown in FIG. 1. The device 26 includes a handle 28 made, e.g., from molded plastic. The handle 28 carries a flexible catheter tube 30. The catheter tube 30 can be constructed, for example, using standard flexible, medical grade plastic materials, like vinyl, nylon, poly(ethylene), ionomer, poly(urethane), poly(amide), and poly(ethylene terephthalate). The handle 28 is sized to be conveniently held by a physician, to introduce the catheter tube 30 into the tissue region targeted for treatment. The catheter tube 30 may be deployed with or without the use of a guide wire (not shown).

The catheter tube 30 carries on its distal end an operative element 36. The operative element 36 can take different forms and can be used for either therapeutic purposes, or diagnostic purposes, or both. The operative element 36 can support, for example, a device for imaging body tissue, such as an endoscope, or an ultrasound transducer. The operative element 36 can also support a device to deliver a drug or therapeutic material to body tissue. The operative element 36 can also support a device for sensing a physiological characteristic in tissue, such as electrical activity, or for transmitting energy to stimulate tissue or to form lesions in tissue.

In the illustrated embodiment (shown in greater detail in FIGS. 2, 3, and 4), one function that the operative element 36 performs is to apply energy in a selective fashion to a targeted tissue region. For the purpose of illustration, the targeted tissue region can comprise, for example, the lower esophageal sphincter, or cardia of the stomach, or both. The applied energy creates one or more lesions, or a prescribed pattern of lesions, below the mucosal surface of the esophagus or cardia. The subsurface lesions are formed in a manner that preserves and protects the mucosal surface against thermal damage. The natural healing of the subsurface lesions leads to a physical tightening of the sphincter and/or adjoining cardia. The subsurface lesions can also result in the interruption of aberrant electrical pathways that may cause spontaneous sphincter relaxation. In any event, the treatment can restore normal closure function to the sphincter.

In this arrangement (as FIG. 1 shows), the treatment device 26 can operate as part of a system 24. The system 24 includes a generator 38 to supply the treatment energy to the operative element 36.

A cable 40 is coupled to the handle 28. The cable 40 is electrically coupled to the operative element 36 by wires that extend through the catheter tube 30. The cable 40 is also electrically coupled to the generator 38, to convey the generated energy to the operative element 36.

In the illustrated embodiment, the generator 38 supplies radio frequency energy, e.g., having a frequency in the range of about 400 kHz to about 10 mHz. Of course, other forms of energy can be applied, e.g., coherent or incoherent light;

heated or cooled fluid; resistive heating; microwave; ultrasound; a tissue ablation fluid; or cryogenic fluid.

The system 24 can also include certain auxiliary processing equipment. In the illustrated embodiment, the processing equipment comprises an external fluid delivery or irrigation apparatus 44. A luer fitting 48 on the handle 28 couples to tubing 34 to connect the treatment device 26 to the fluid delivery apparatus 44, to convey processing fluid for discharge by or near the operative element 36.

The system 24 also desirably includes a controller 52. The controller 52 is linked to the generator 38 and the fluid delivery apparatus 44. The controller 52, which preferably includes an onboard central processing unit, governs the power levels, cycles, and duration that the radio frequency energy is distributed to the operative element 36, to achieve and maintain power levels appropriate to achieve the desired treatment objectives. In tandem, the controller 52 also desirably governs the delivery of processing fluid.

The controller 52 desirably includes an input/output (I/O) device 54. The I/O device 54 allows the physician to input control and processing variables, to enable the controller to generate appropriate command signals.

II. The Operative Element

Figure 2:
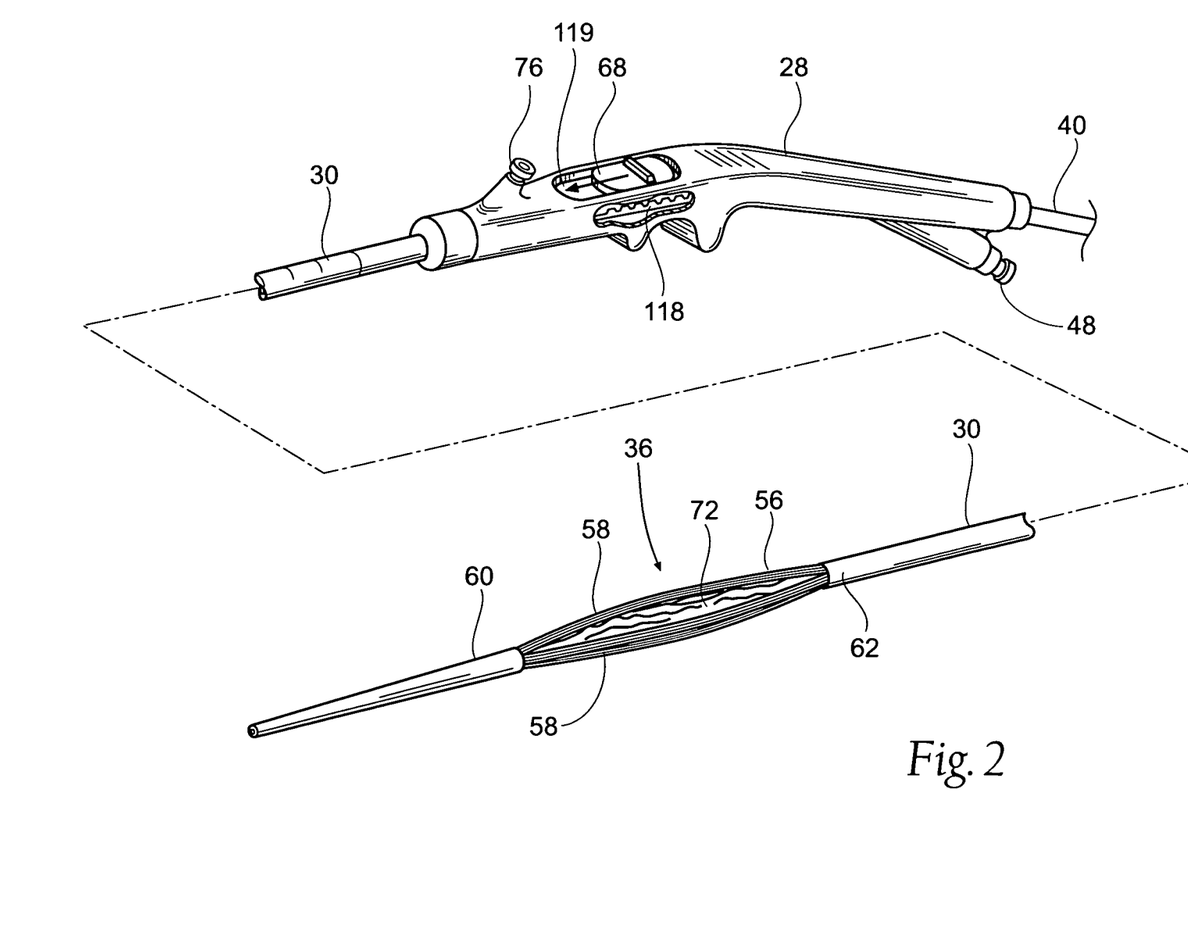
FIG. 2 is a perspective view, with portions broken away and in section, of the treatment device shown in FIG. 1, with the basket element carried by the device shown in a collapsed condition for deployment to a targeted tissue region.
Figure 3:
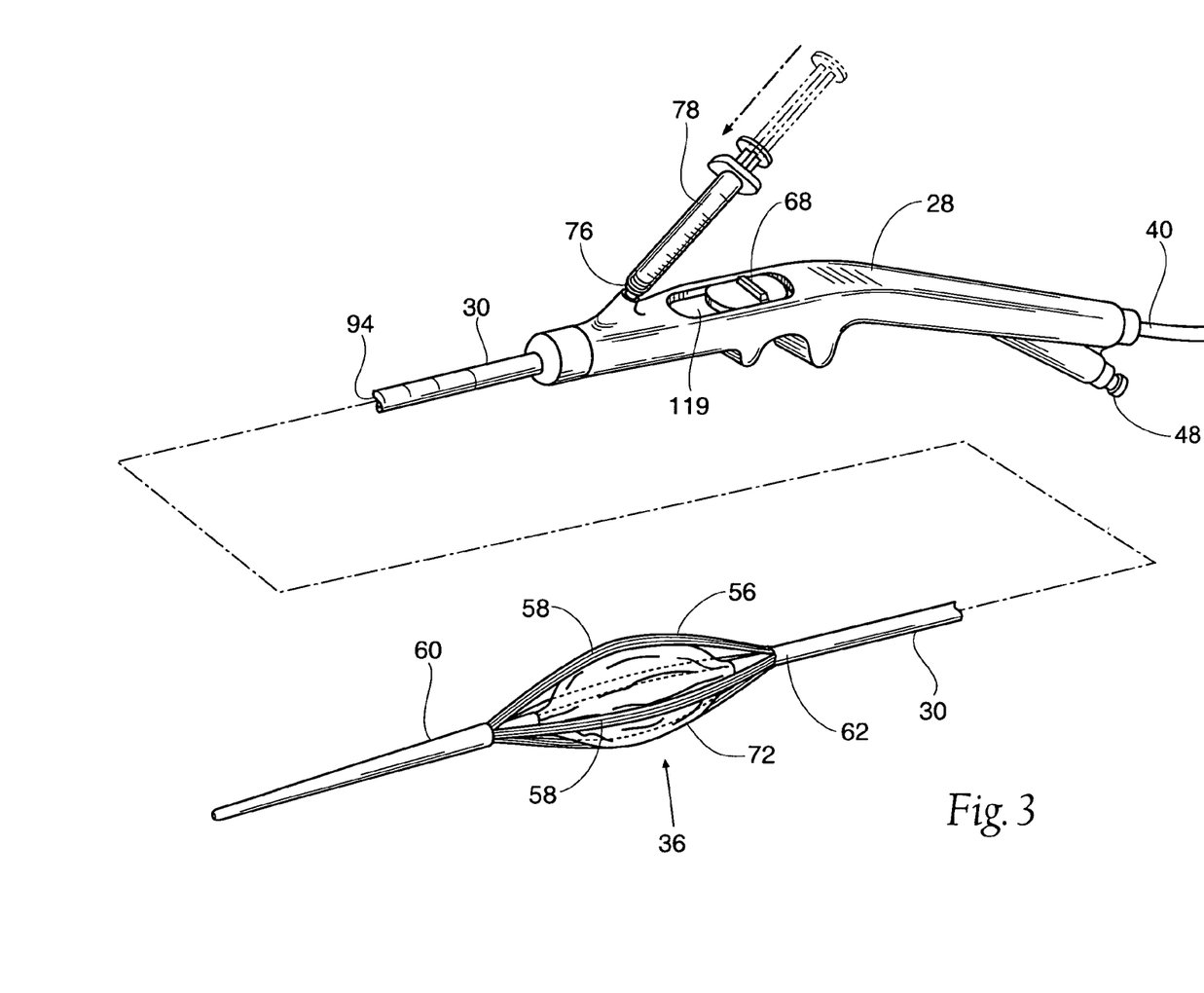
FIG. 3 is a perspective view, with portions broken away, of the treatment device shown in FIG. 1, with the basket element carried by the device shown in an expanded condition, as it would be when ready for use in a targeted tissue region.
Figure 4:
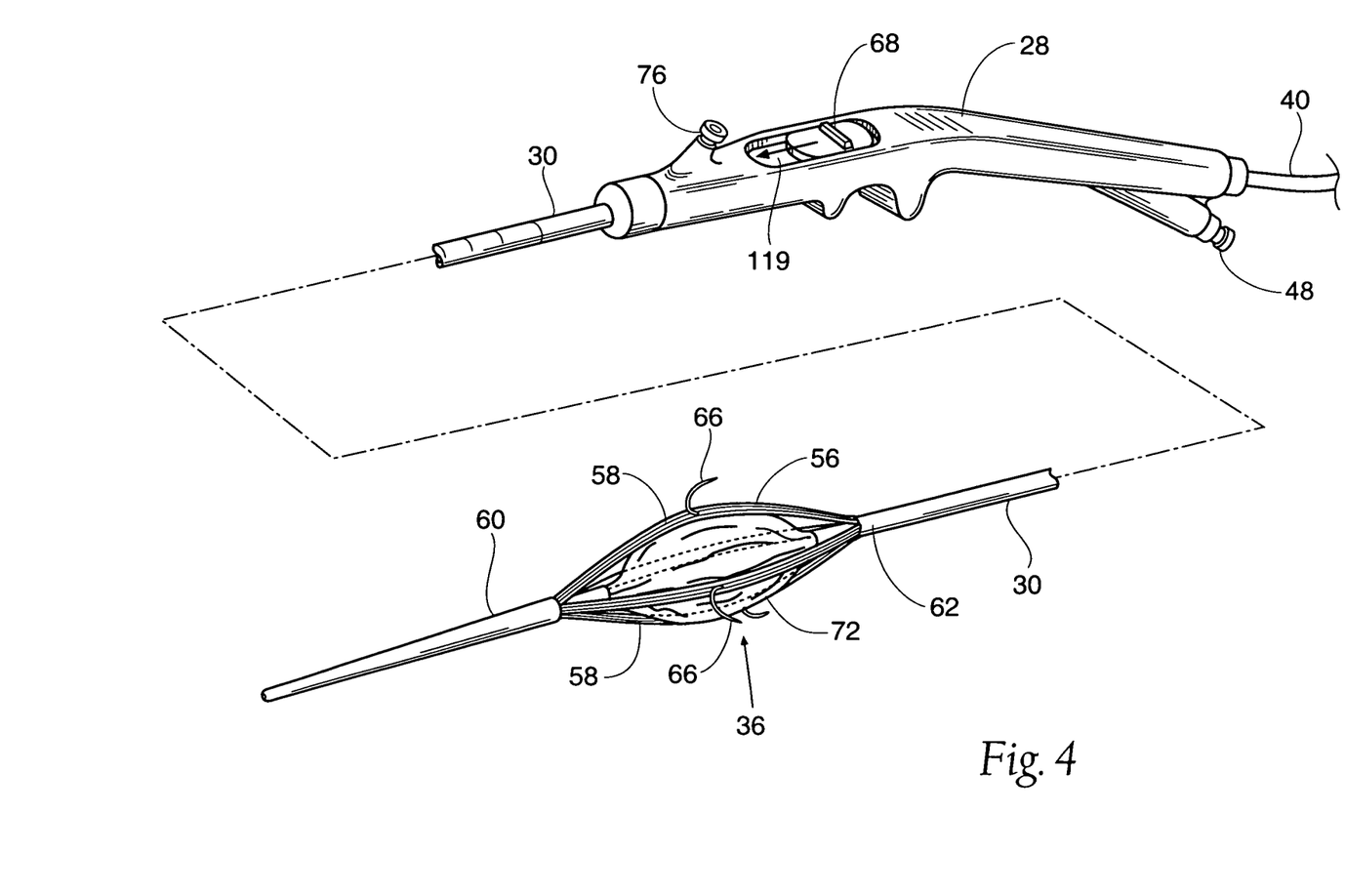
FIG. 4 is a perspective view, with portions broken away, of the treatment device shown in FIG. 1, with the basket element carried by the device shown in an expanded condition, and with electrodes carried by the basket element extended for use in a targeted tissue region.

In the embodiment shown in FIGS. 2 to 4, the operative element 36 comprises a three-dimensional basket 56. The basket 56 includes one or more spines 58, and typically includes from four to eight spines 58, which are assembled together by a distal hub 60 and a proximal base 62. In FIGS. 2 to 4, four spines 58 are shown, which are equally circumferentially spaced apart.

Each spine 58 preferably comprises a flexible body made, e.g. from molded plastic, stainless steel, or nickel titanium alloy. Candidate plastic materials for the spine 58 include PEEK, Ultem, polyimide, Pebax, Hytrel polyester, PET, and polyurethane.

The cross sectional shape of the spine body 58 can vary, possessing, e.g., a circular, elliptical, square, or rectilinear shape. In the illustrated embodiment, the spine bodies 58 each possess a rectilinear shape to resist twisting.

Figure 5:
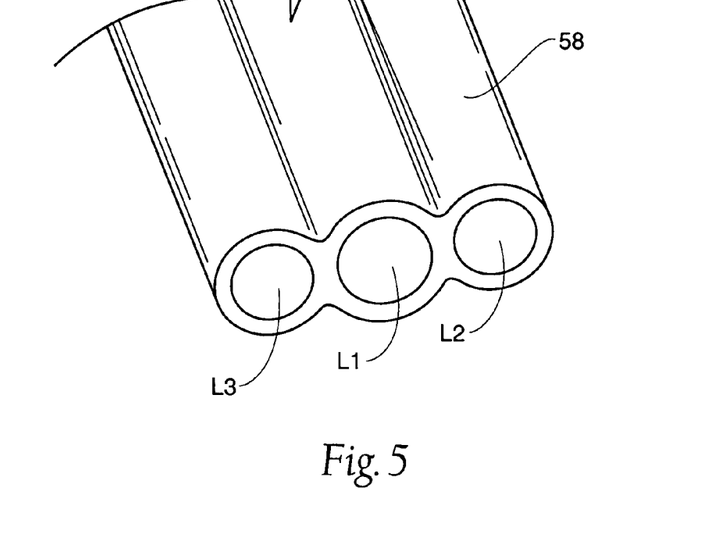
FIG. 5 is an enlarged end view of one of the multiple lumen spines that form the basket element shown in FIGS. 2 to 4, showing the multiple interior lumens that the spine possesses.

In the illustrated embodiment (see FIG. 5), each spine body 58 defines two or more interior lumens or passages. As FIG. 5 shows, in the illustrated embodiment, three lumens or passages, designated L1, L2, and L3, are present. For each spine 58, each passage L1, L2, and L3 is dedicated to accommodate a different functional element.

In the illustrated embodiment (see FIGS. 6 and 7), a first or center passage L1 carries a movable, elongated electrode element 66. A second passage L2 along one side the first passage L1 carries a temperature sensing element 80. A third passage L3 along the opposite side of first passage L1 is coupled to tubing 82 that carries processing fluid from the fluid delivery device 44.

A. The Electrodes

Figure 8:
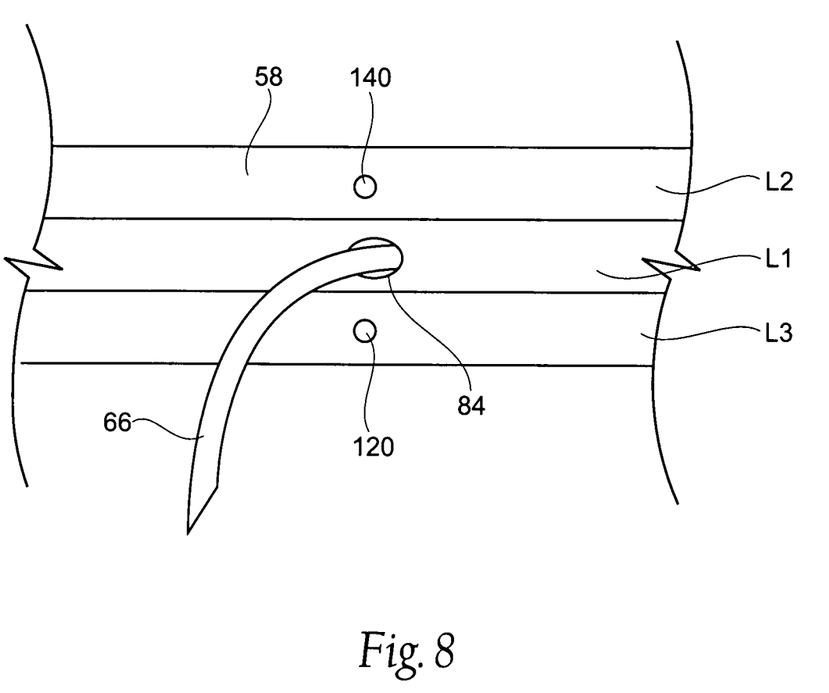
FIG. 8 is an enlarged view of a portion of one of the multiple lumen spines that form the basket element shown in FIGS. 2 to 4, showing an electrode deployed through an opening in one of the spines.

Each electrode 66 is carried within the first passage L1 for sliding movement. Each electrode 66 slides from a retracted position, withdrawn in the spine 58 (as shown in FIG. 3), and an extended position, extending outward from the spine 58 through an opening 84 in the spine 58 (as shown in FIGS. 4 and 8).

Figure 7:
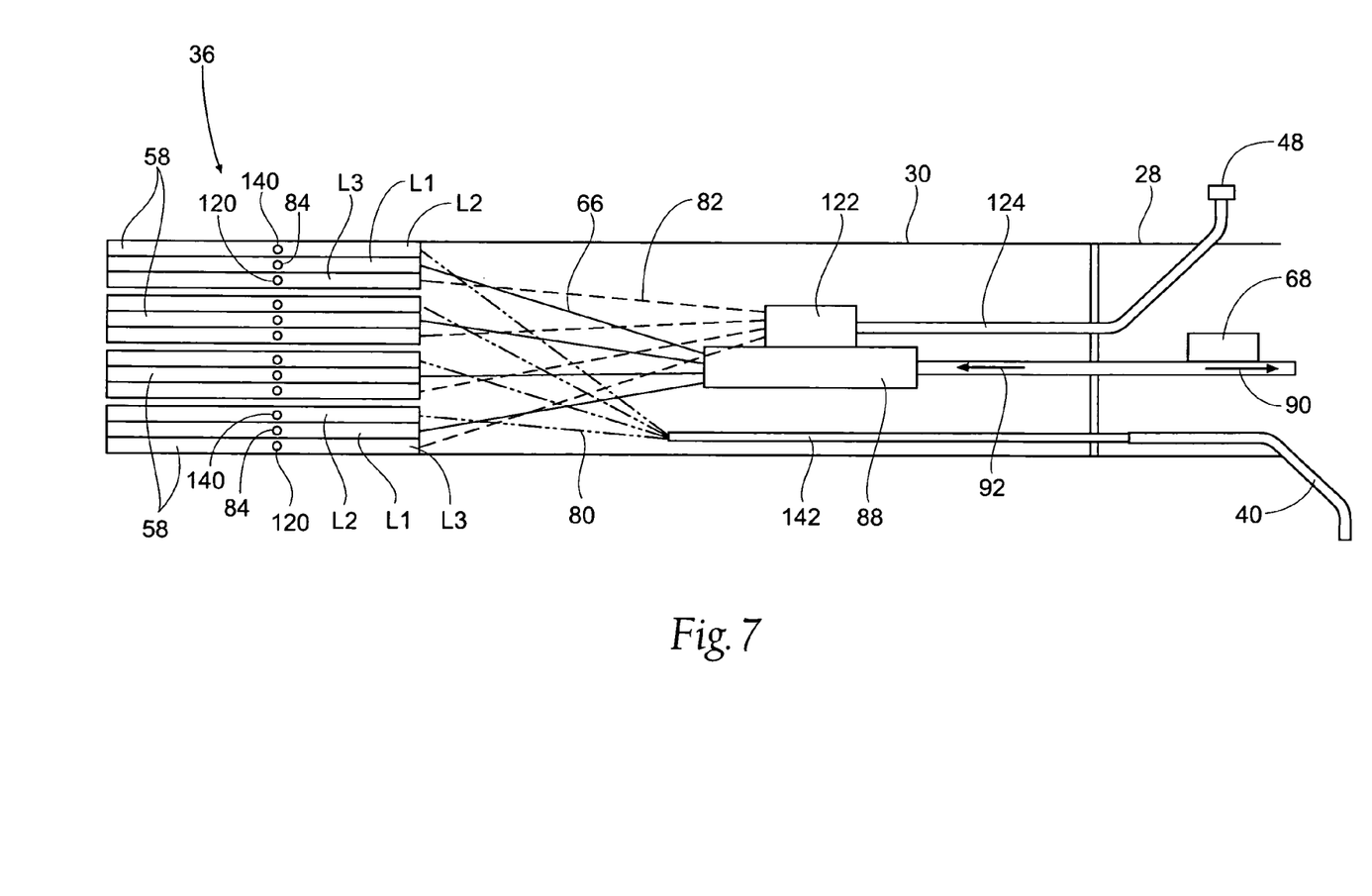
FIG. 7 is a schematic view of the interior of the catheter tube and handle of the treatment device shown in FIGS. 2 to 4, showing the routing of different functional elements within the confined space of the catheter tube.

As FIG. 7 best shows, a push-pull lever 68 on the handle 28 (as FIGS. 2 to 4 also show) is coupled by a stylet 86 to a carrier 88 located within the catheter tube 30. The electrodes 66 are secured to the carrier 88, extending from the carrier 88 into the lumens L1 of the respective spine 58. The lever 68 controls the sliding movement of the electrodes with the spines 58 between the retracted position (by pulling rearward on the lever 68, arrow 90 in FIG. 7) and the extended position (by pushing forward on the lever 68, arrow 92 in FIG. 7).

As FIGS. 2 to 4 show, the lever 68 is exposed on the handle 28 for manipulation by the thumb of an operator. A suitable rachet assembly 118 (see FIG. 2) may be provided to advance the sliding movement of the lever 68 in a controlled, stepwise fashion. A slot 119 on the handle 28 stops advancement of the lever 68 beyond a predetermined distance.

In the illustrated arrangement, the electrodes 66 are intended for monopolar operation. Each electrode 66 serves as a transmitter of energy, and an indifferent patch electrode on the patient=s skin (not shown) serves as a common return for all electrodes 66. It should be appreciated, however, the operative element 36 could include bipolar pairs of electrodes 66, if desired.

In the embodiment shown in FIGS. 2 to 4, an expandable structure 72 comprising, e.g., a balloon, is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in-contact with tissue. Compliant materials offer the advantages of variable sizes and shape conformance to adjacent tissue geometries.

The balloon structure 72 presents a normally, generally collapsed condition, as FIG. 2 shows. In this condition, the basket 56 is also normally collapsed about the balloon structure 72, presenting a low profile for deployment into the targeted tissue region.

The catheter tube 30 includes an interior lumen 94 (see FIG. 3), which communicates with the interior of the balloon structure 72. A fitting 76 (e.g., a syringe-activated check valve) is carried by the handle 28. The fitting 76 communicates with the lumen. The fitting 76 couples the lumen 94 to a syringe 78 (see FIG. 3), which injects fluid under pressure through the lumen 94 into the balloon structure 72, causing its expansion, as FIG. 3 shows.

Expansion of the balloon structure 72 urges the spines 58 of the basket 56 to open and expand (as FIG. 3 shows). The force exerted by the balloon structure 72 upon the spines 58, when expanded, is sufficient to exert an opening force upon the tissue surrounding the basket 56. When moved to their extended positions, the electrode 66 penetrate tissue contacted by the spines 58.

The electrodes 66 can be formed from various energy transmitting materials. For deployment in the esophagus or cardia of the stomach, the electrodes 66 are formed, e.g., from nickel titanium. The electrodes 66 can also be formed from stainless steel, e.g., 304 stainless steel, or, as will be described later, a combination of nickel titanium and stainless steel. The electrodes 66 have sufficient distal sharpness and strength to penetrate a desired depth into the smooth muscle of the esophageal or cardia wall. The desired depth can range from about 4 mm to about 5 mm.

To further facilitate penetration and anchoring in the targeted tissue region, each electrode 66 is preferably biased with a bend (as FIGS. 4 and 8 show). Movement of the electrode 66 into the spine 58 overcomes the bias and straightens the electrode 66 for passage through the lumen L1.

In the illustrated embodiment (see FIGS. 4 and 8), each electrode 66 is normally biased with an antegrade bend (i.e., bending toward the proximal base 62 of the basket 56). Alternatively, each electrode 66 can be normally biased toward an opposite retrograde bend (i.e., bending toward the distal hub 60 of the basket 58).

Figure 9:
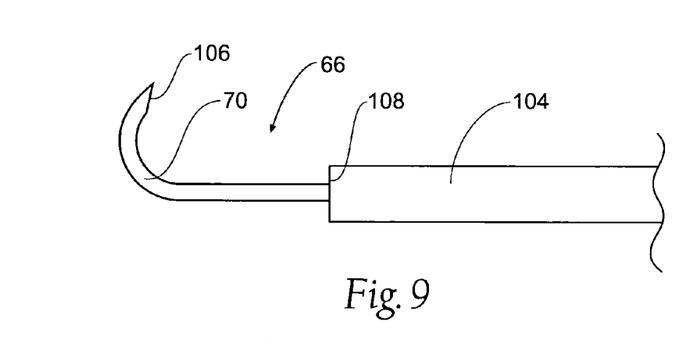
FIG. 9 is a side view of the electrode shown in FIG. 8, out of association with the spine.

An electrical insulating material 70 (see FIG. 9) is desirably coated about the distal end of each electrode 66, a distance below the distal tip. For deployment in the esophagus or cardia, the length of the insulating material 70 ranges from about 80 to about 120 mm. The insulating material can comprise, e.g., a Polyethylene Terephthalate (PET) material, or a polyimide or polyamide material. For deployment in the esophagus or cardia, each electrode 66 preferably presents an exposed, non-insulated conductive length of about 8 mm. When the distal end of the electrode 66 that penetrates the targeted tissue region transmits radio frequency energy, the material 70 insulates the surface of the tissue region from direct exposure to the radio frequency energy.

Desirably (see FIG. 10), the electrode 66 slides within an insert 96 positioned within the first passage L1. The insert 96 guides the electrode 66 to the electrode opening 84 and protects the spine 58 from inadvertent puncture or Apokethrough@ by the electrode 66.

The insert 96 is preferably made of a relatively hard (i.e., high durometer) and tough plastic material, e.g., PEEK plastic. This plastic material has a durometer in excess of 75 Shore D. The hardness provides lubricity for easy electrode movement within the insert 96, and the toughness makes the insert 96 resistant to puncture by the electrode 66. The insert material desirably is also adhesively bondable, which PEEK plastic is. Desirably, the insert is also reformable with heat, which PEEK plastic is, so that its outer diameter can be readily altered in desired ways during manufacture, as will be described in greater detail below.

Other candidate materials for the insert 96 include Ultem, polyimide, Pebax, Hytrel polyester, PET, and polyurethane.

A main advantage of the insert 96 is absolute guidance of the electrode 66 through the spine opening 84. The flexibility to provide an insert 96 of a different material and possessing different mechanical properties than a spine 58 is another advantage. The insert 96 can also have a different wall thickness than the spine body 58, so that the dimensions of each of these components can be made appropriate to the function they perform.

Figure 10:
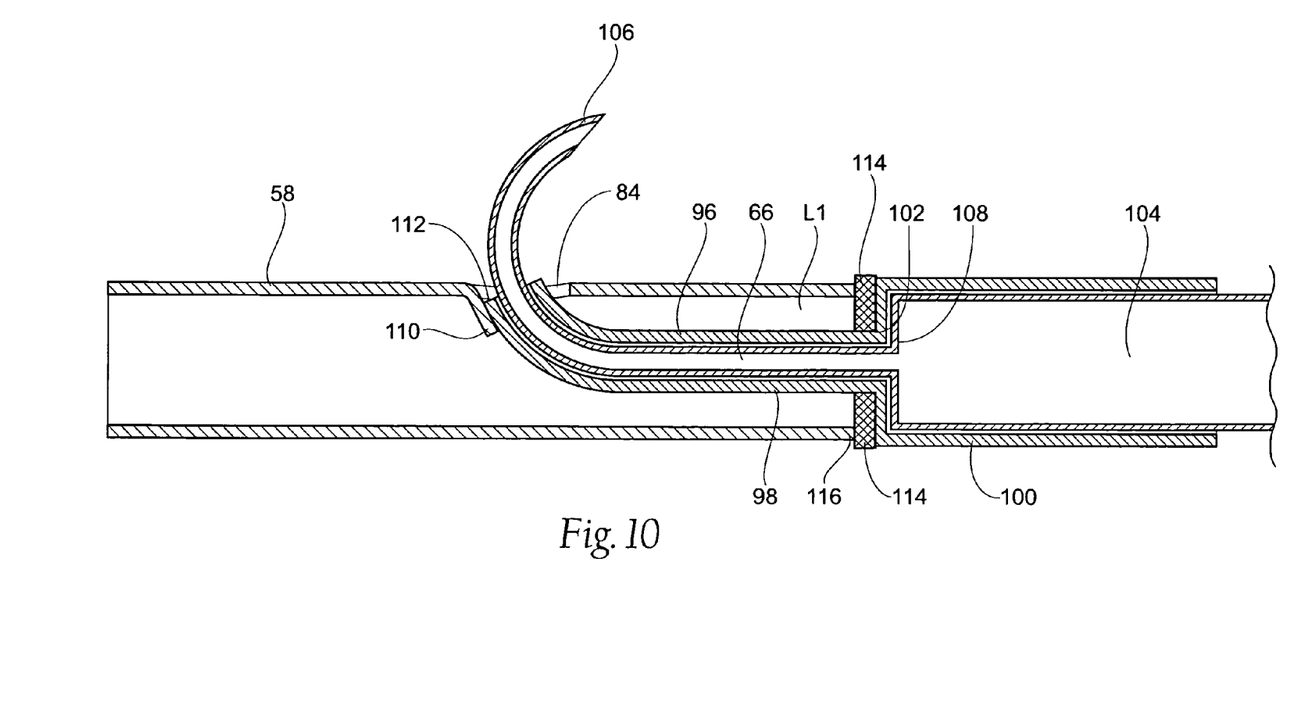
FIG. 10 is a side section view of the lumen of the spine shown in FIG. 5, in which the electrode shown in FIG. 9 is carried, showing an insert that guides passage of the electrode within the spine, and showing the electrode in an extended position for use.

As FIG. 10 shows, the insert 96 includes a first body portion 98 and a second body portion 100. The first body portion 96 has an outside diameter smaller than the inner diameter of the passage L1, to accommodate insertion of the first body portion 98 into the passage L1. The second body portion 100 has an outside diameter that is larger than the inner diameter of the passage L1, to prevent its insertion into the passage. The transition between the first and second body portions 98 and 100 forms a notch 102 that abuts against the proximal end 116 of the spine 58. This abutment forms a mechanical stop, to prevent movement of the first body portion 98 within the passage L1 beyond a prescribed distance.

In this arrangement (see FIG. 9), the electrode 66 may comprise a hybrid of materials comprising stainless steel for the proximal portion 104 and nickel titanium alloy for the distal portion 106. The nickel titanium alloy performs best in the curved distal portion 106 of the electrode 66, due to its super-elastic properties. The use of stainless steel in the proximal portion 104 can reduce cost, by minimizing the amount of nickel titanium alloy required.

The different materials may be joined, e.g., by crimping, swaging, soldering, welding, or adhesive bonding, which provide electrical continuity between or among the various materials.

The distal portion 106 of the electrode 66 possesses an outside diameter less than the inner diameter of the insert 96. This allows the distal portion 106 of the electrode 66 to freely slide within the insert 96. The proximal portion 104 of the electrode has an outside diameter that is larger than the inner diameter of the insert 96. The transition between the distal and proximal portions 106 and 104 of the electrode 66 forms a notch 108 that abuts against the notch 102 formed at the transition between the first and second body portions 98 and 100 of the insert 96.

Figure 11:
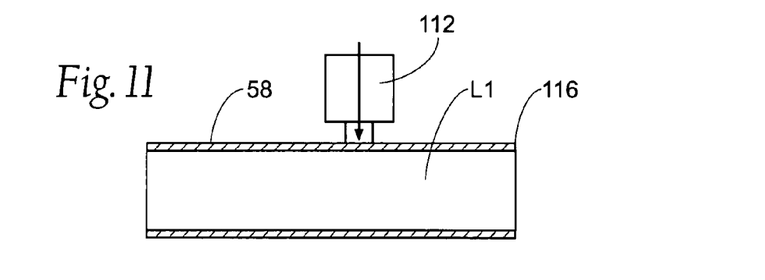
FIGS. 11 to 15 are side sectional views showing the assembly of the insert shown in FIG. 10 into the spine.
Figure 12:
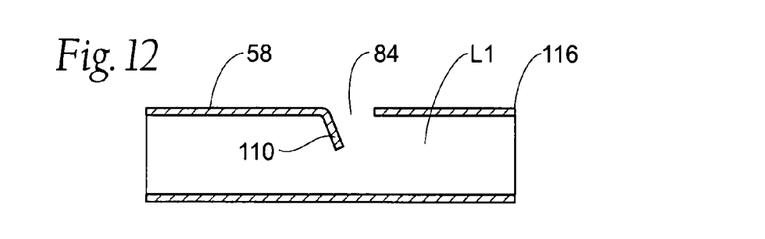

In assembly (see FIG. 11), the electrode opening 84 is formed in the spine 58 by a heat gun 112 or the like in the desired located on the exterior of the passage L1. As FIG. 12 shows, a segment 110 of the spine wall is displaced into the passage L1 as the opening 84 is created. This wall segment 110 is deflected into the passage L1, to form an interior ramp appended to the opening 84.

Figure 13:
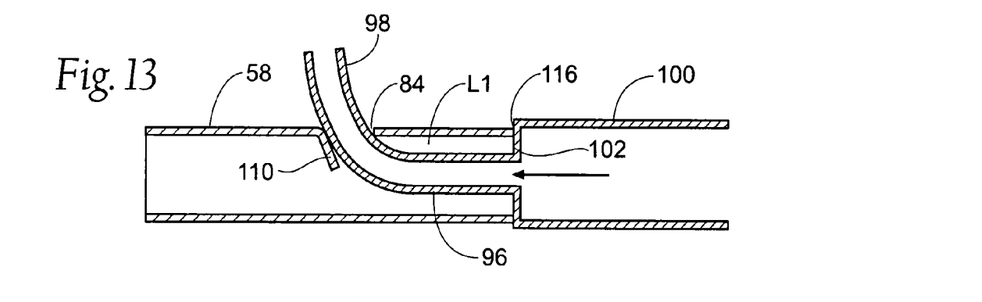

As FIG. 13 shows, the first body portion 98 of the insert 96 is inserted through the proximal end 116 of the spine 58 into the passage L1. The first body portion 98 is advanced through the formed opening 84 to the fullest extent permitted, i.e., until the notch 102 between the first and second body portions 98 and 100 abuts against the proximal end 116 of the spine 58.

Figure 14:
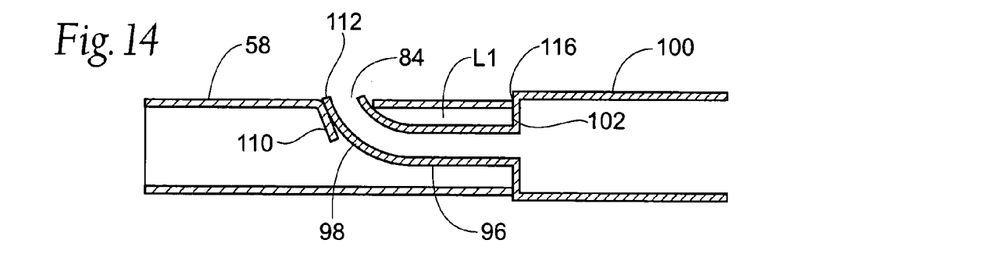
Figure 15:
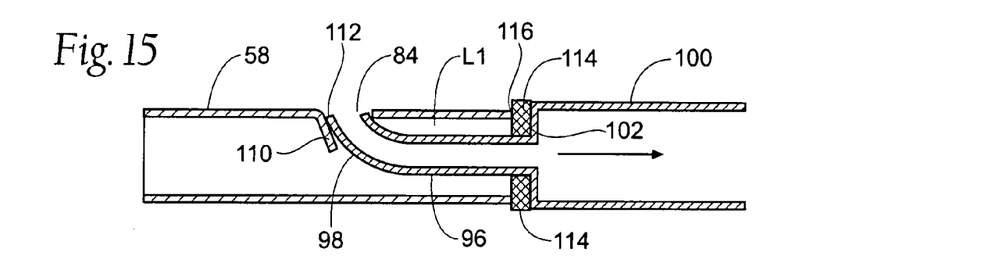
Figure 16:
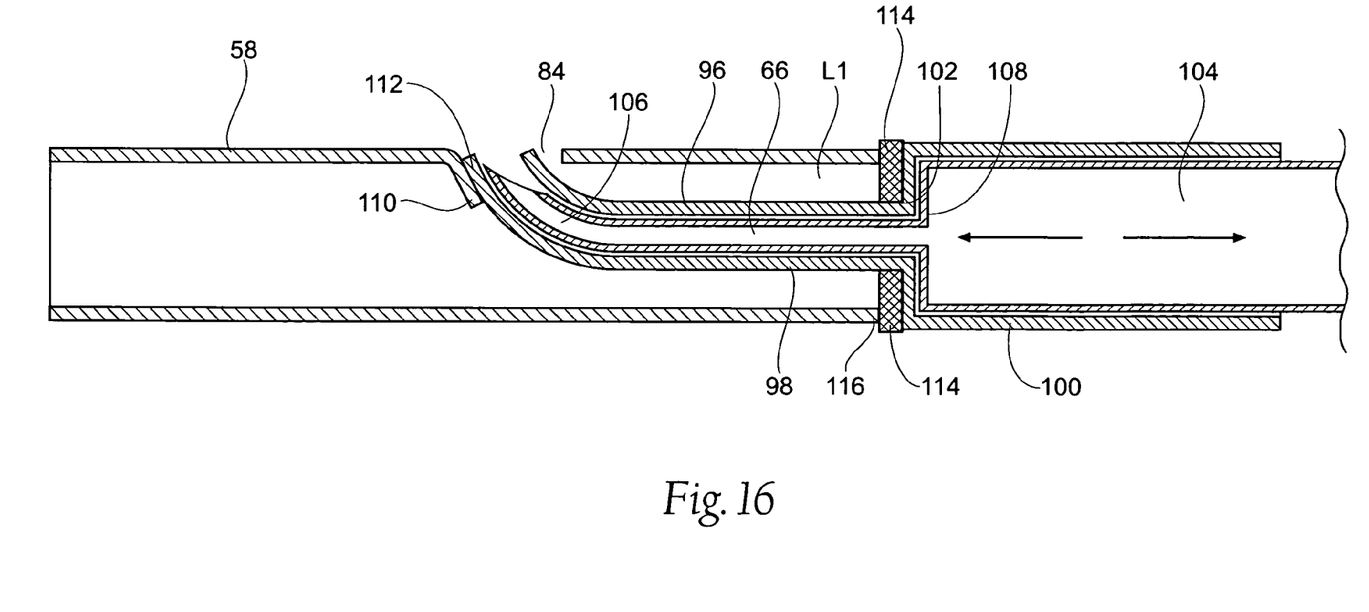
FIG. 16 is a side section view of the lumen of the spine shown in FIG. 10, showing the electrode in a retracted position within the insert.
Figure 17:
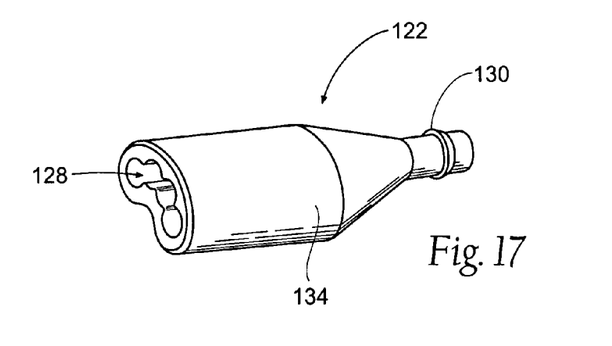
FIG. 17 is a perspective view of an irrigation manifold that the treatment device shown in FIG. 1 possesses, to route fluid within the catheter tube from a single source to several basket spines.
Figure 18:
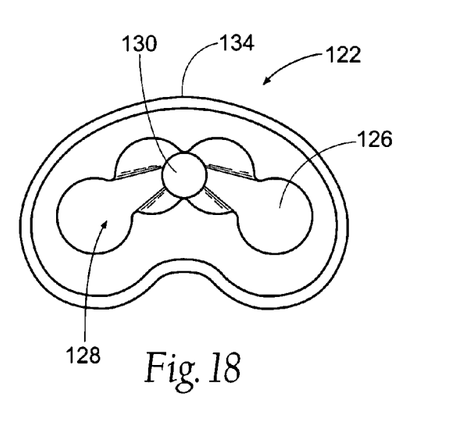
FIG. 18 is a distal end view of the irrigation manifold shown in FIG. 17.
Figure 19:
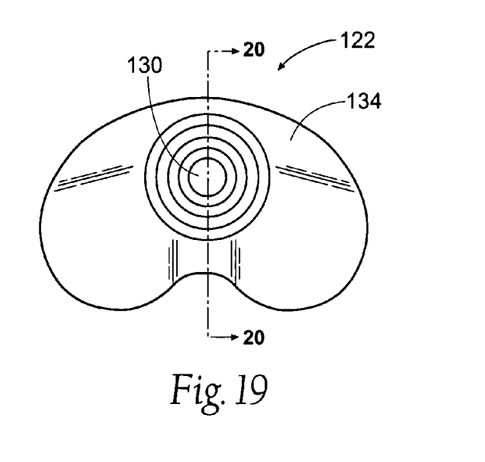
FIG. 19 is a proximal end view of the irrigation manifold shown in FIG. 17.
Figure 20:
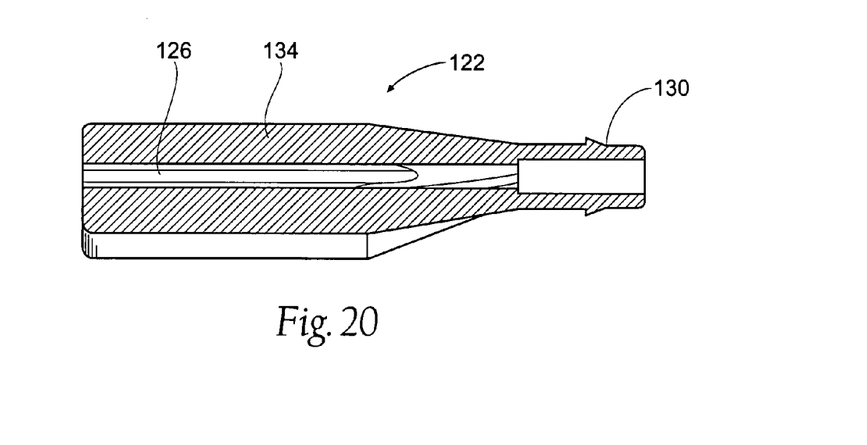
FIG. 20 is a side section view of the irrigation manifold shown in FIG. 17 taken generally along line 20-20 in FIG. 19.

As FIG. 14 shows, the first body portion 98 that projects from the opening 84 is cut to form a terminus 112 that is flush with the opening 84. The insert 96 is then pulled back a small distance (see FIG. 15), so that the terminus 112 rests within the passage L1 against the ramp wall segment 110, a small distance below the plane of the opening 84. Adhesive 114 is applied in the space between the notch 102 and the proximal end 116 of the spine 58, to thereby secure the insert 96 to the body of the spine 58. As FIG. 16 shows, the distal portion 106 of the electrode 66 freely slides through the insert 96 in response to operation of the push-pull lever 68 previously described. The insert terminus 112 faces toward the opening 84, and serves to reliably guide the distal portion 106 of the electrode 66 toward and away from the opening 84. The eventual abutment between the lever 68 and the slot 119 on the handle 28 (see FIG. 2) will mechanically stop further passage of the distal portion 106 of the electrode 66 through the opening 84. The depth of electrode penetration into tissue is thus mechanically controlled, to prevent puncture through the targeted tissue region.

Should the adhesive 114 fail, the eventual abutment of the notch 102 (between the first and second body portions 98 and 100 of the insert 96) against the proximal end 116 of the spine 58 will mechanically limit the extent to which the insert terminus 112 can advance through the opening 84. The mechanically limited displacement of the insert terminus 112 through the opening 84 serves to prevent exposure of the cut insert terminus 112 beyond the plane of the electrode opening and into contact with tissue.

The electrodes 66 can be formed in various sizes and shapes. The electrodes 66 can possess a circular cross sectional shape. However, the electrodes 66 preferably possess a cross section that provides increased resistance to twisting or bending as the electrodes penetrate tissue. For example, the electrodes 66 can possess a rectangular cross section. Alternatively, the electrodes 66 can possess an elliptical cross section. Other cross sections, e.g., conical or pyramidal, can also be used to resist twisting.

The surface of the electrode 66 can, e.g., be smooth, or textured, or concave, or convex. The preceding description describes electrodes 66 bent in either an antegrade or retrograde direction over an arc of ninety degrees or less. The bend provides a secure anchorage in tissue. Retraction of the electrodes 66 into the insert overcomes the bias and straightens the electrode 66 when not in use.

B. Surface Cooling

In the illustrated embodiment (see FIG. 6), the fluid delivery apparatus 44 conveys processing fluid through the third passage L3 in the spine 58 for discharge at the treatment site. The processing fluid F can comprise, e.g., saline or sterile water, to cool surface tissue while energy is being applied by the electrode 66 to ohmically heat muscle or tissue beneath the surface, to thereby protect the surface tissue from thermal damage.

The third passage L3 conveys liquid from the irrigation apparatus through an opening 120 formed in the spine 58. The irrigation opening 120 in each spine 58 is generally aligned with the needle opening 84 in the spine 58, so that ablation and cooling occur in the same general tissue region.

Figure 21:
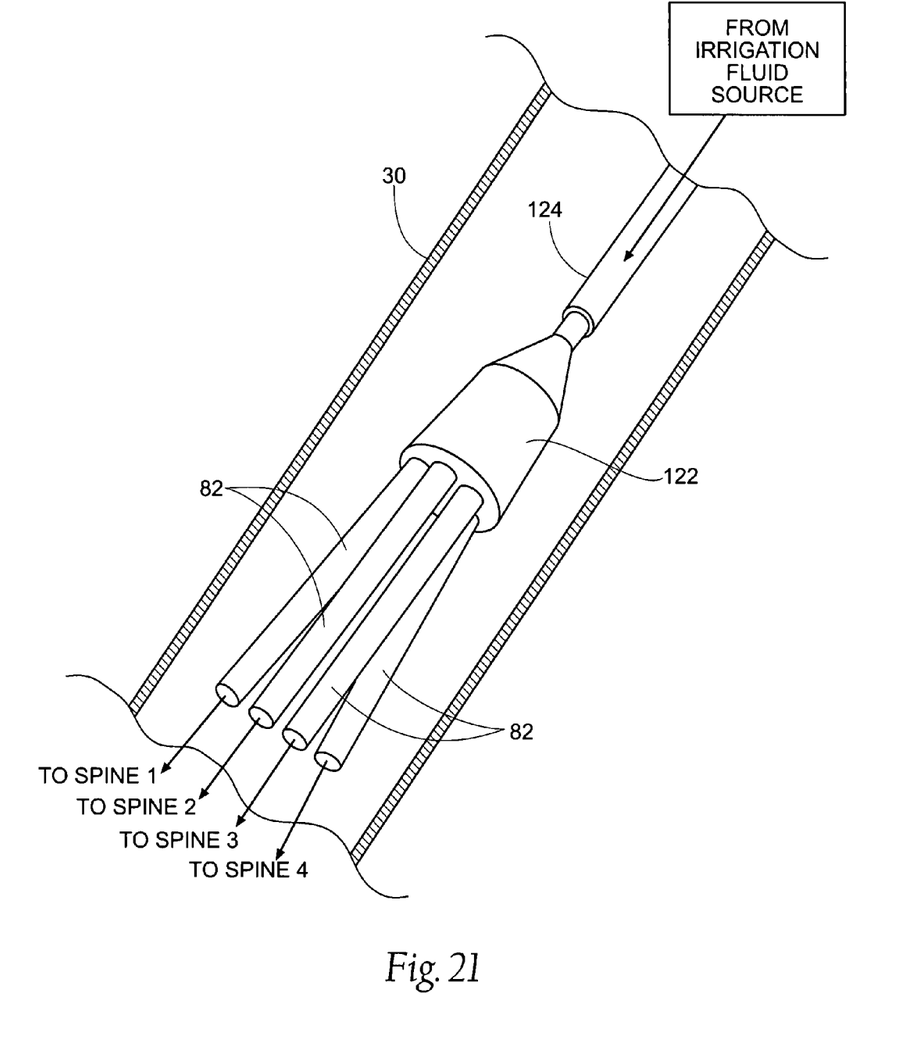
FIG. 21 is a schematic view of the irrigation manifold shown in FIG. 17 positioned within the catheter tube of the treatment device shown on FIG. 1, and serving to channel fluid from a source simultaneously to several basket spines.

In the illustrated embodiment (see FIG. 7), the individual lengths of tubing 82 that convey irrigation fluid to each passage L3 of the spines 58 are coupled to an irrigation manifold 122 within the catheter tube 30. The irrigation manifold 122 is, in turn, coupled by a single tube 124 to the luer fitting 48 on the handle 28, previously described (see FIG. 1). The irrigation manifold 122 simplifies connection of the multiple tubing 82 to the single tube 124 within the confined space of the catheter tube 30 (as FIG. 21 shows), as well as efficiently routes cooling fluid to the appropriate openings 120.

The irrigation manifold 122 can be constructed in various ways, e.g., from molded or machined plastic such as polycarbonate or Ultem. In the illustrated embodiment (see FIGS. 17 to 20), the manifold 122 is formed from plastic to form a compact body 134 sized to fit within the catheter tube. The manifold body including a single main fluid junction or inlet port 130, multiple branch fluid junctions or apertures 128, and a fluid circuit 126 formed within the manifold body 134 to channel fluid flow between the single main fluid junction 130 and the multiple branch fluid junctions 128. The single tube 124 is secured to the main fluid junction 130 (see FIG. 21), e.g., by an adhesive bond. The multiple branch fluid junctions or apertures 128, which are sized and arranged side-by-side to receive individual ends of the tubings 82 (see FIG. 21), e.g., by adhesive bonds. The apertures 128 desirably include internal tubing stops to facilitate accurate adhesive bonding. The manifold 122 is also desirably made from a clear or transparent plastic, to further facilitate the process of adhesive bonding the tubings 82 within the apertures 128. The tubings 82 extend from the manifold 122 and are routed to the designated passages L3 in the spines 58. The cavity 126 distributes irrigation fluid conveyed through the single tube 124 to the individual tubings 82 serving the spines 58.

In a representative embodiment, the manifold body 134 can measure about 0.74 inch in overall maximum length (from apertures 128 to the end of the inlet port 130) and about 0.274 inch in maximum width.

It should be appreciated that the manifold 122 can serve to handle fluid flow either to (i.e, fluid irrigation) or from (i.e., fluid aspiration) an operative element carried by a catheter tube. The manifold body for carrying out either function is sized to fit within the catheter tube. The manifold body is machined or molded as a single unit to including a single main fluid junction (inlet 130), multiple branch fluid junctions (apertures 128), and a fluid circuit (circuit 126) to channel fluid flow between the single main fluid junction and the multiple branch fluid junctions. The single main fluid junction can be coupled either to a fluid source or a fluid destination external to the catheter tube. Likewise, each of the multiple branch fluid junctions can be individually coupled to a fluid-conveying port on the operative element.

C. Temperature Sensing

Figure 6:
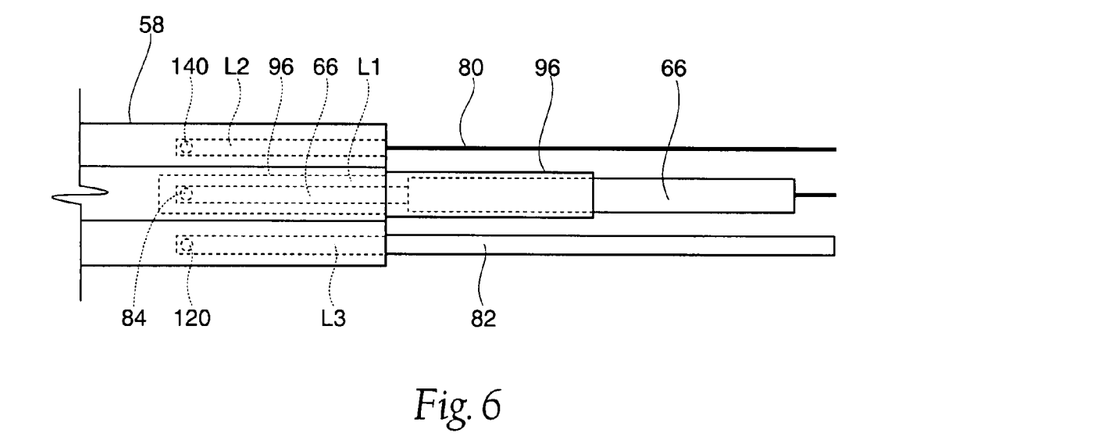
FIG. 6 is a top view of the multiple lumen spine shown in FIG. 5, showing the different functional elements that the interior lumens of the spine carry.

In the illustrated embodiment (see FIGS. 6 and 7), the second passage L2 in each spine 58 carries a temperature sensing element 80. In the illustrated embodiment, the temperature sensing element 80 comprises a thermocouple assembly. The temperature sensor is exposed through an opening 140 in the spine body 38. The temperature sensor rests against surface tissue when the basket structure is deployed for use. Desirably (as FIG. 6 shows), the temperature sensor opening 140 is generally aligned with the electrode and cooling fluid openings 84 and 120, so that ablation, temperature sensing, and cooling occur generally in the same localized tissue region.

As FIG. 7 shows, the individual thermocouple wires 80 extend from the respective passages L2. The thermocouple wires 80 are desirably wound to form a composite thermocouple cable 142. The thermocouple cable 142 extends through the catheter tube 30 into the handle 28. The thermocouple cable 142 is electrically coupled (via the cable 40) to temperature sensing and processing elements of the controller 52.

The I/O device 54 of the controller 52 receives real time processing feedback information from the temperature sensors 80, for processing by the controller 52, e.g., to govern the application of energy and the delivery of processing fluid. The I/O device 54 can also include a graphical user interface (GUI), to graphically present processing information to the physician for viewing or analysis.

Various features of the invention are set forth in the following claim.

We claim:

1. A method of handling fluid flow to or from an operative element carried by a catheter tube comprising the steps of
   providing a manifold body sized to fixedly fit within the catheter tube, the manifold body including a single main fixed fluid junction, multiple branch fluid junctions, and a fluid circuit formed within the manifold body to channel fluid flow between the single main fluid junction and the multiple branch fluid junctions,
   wherein said operative element includes a basket structure comprising at least first and second spines, each spine including a flexible body defining at least two interior first and second lumens, a first one of the interior lumens of each first and second spine including a fluid-conveying port,
   coupling the single main fluid junction to a fluid source or a fluid destination external to the catheter tube,
   coupling each of the multiple branch fluid junctions individually to said fluid-conveying port on the operative element, and
   mounting the manifold within the catheter tube.

2. A device for treating body tissue comprising:
   a handle;
   a tube extending from the handle;
   an operative element extending from a distal portion of the tube, the operative element including a plurality of spines, the spines having an electrode lumen and a fluid lumen, the fluid lumen fluidly coupled to a fluid tubing for passage of fluid through the fluid lumen into the body tissue;
   an electrode slidably positioned in the electrode lumen of the spines for movement from a retracted position to an extended position; and
   a fixed irrigation manifold having an inlet port, multiple apertures, and a fluid circuit between the inlet port and apertures, the fluid tubings coupled to the fluid lumens of the spines at a first end and coupled to the manifold at a second opposite end, and the irrigation manifold is coupled to a single fixed tube at the inlet port to fluidly couple the single tube to the fluid tubings.

3. The device of claim 2, wherein the manifold is positioned within the tube.

4. The device of claim 2, wherein the manifold is made of transparent material.

5. The device of claim 2, wherein the spines include a sensing lumen for carrying a temperature sensing element.

6. The device of claim 5, wherein the temperature sensing element comprises a thermocouple assembly and the sensing element is exposed through an opening in the spine.

7. The device of claim 5, wherein the electrode lumen is positioned between the fluid lumen and the sensing lumen.

8. The device of claim 2, further comprising a cable electrically coupled to the electrodes and electrically coupled to a generator to convey energy to the electrodes.

9. The device of claim 2, wherein the electrodes are biased with a bend and the electrodes are straightened within the electrode lumens for passage therethrough.

10. The device of claim 2, wherein the spines include an electrode opening in a sidewall to allow for passage of the electrode from the spine when the electrode is moved to the extended position, the electrodes having a penetrating tip to penetrate tissue.

11. The device of claim 2, further comprising an insert positioned within the electrode lumen to guide the electrode.

12. The device of claim 11, wherein the insert is composed of a different material than the spines.

13. The device of claim 11, wherein the insert has a first body portion with an first outside diameter and second a body portion with a second outside diameter larger than the first outside diameter.

14. The device of claim 2, wherein the spines are joined by a distal hub and a proximal hub.

15. The device of claim 10, further comprising an interior ramp adjacent the electrode opening in the spines.

16. The device of claim 2, wherein the spines include a fluid opening in a sidewall communicating with the fluid lumen for passage of fluid into the body tissue.

17. The device of claim 16, wherein the fluid opening is generally aligned with the electrode opening so energy application and cooling are in a same general tissue region.

18. The device of claim 2, wherein the manifold is C-shaped in cross section.

19. The device of claim 2, further comprising a lever on the handle and a carrier within the tube, the lever is coupled to the carrier and the electrodes are secured to the carrier so movement of the lever moves the carrier to move the electrodes to the extended position.

20. The device of claim 2, wherein the apertures of the irrigation manifold are arranged along an arc.

* * * * *